United States Patent
Hübsch et al.

(10) Patent No.: US 6,756,512 B2
(45) Date of Patent: Jun. 29, 2004

(54) METHOD FOR PRODUCING 2-ALKYL-3-CHLOROPHENOLS

(75) Inventors: Walter Hübsch, Wuppertal (DE);
Reinhard Lantzsch, Wuppertal (DE);
Thorsten Müh, Leverkusen (DE);
Holger Weintritt, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/258,900

(22) PCT Filed: Apr. 23, 2001

(86) PCT No.: PCT/EP01/04547
§ 371 (c)(1),
(2), (4) Date: Oct. 30, 2002

(87) PCT Pub. No.: WO01/83417
PCT Pub. Date: Nov. 8, 2001

(65) Prior Publication Data
US 2003/0092944 A1 May 15, 2003

(30) Foreign Application Priority Data
May 3, 2000 (DE) .......................... 100 21 413

(51) Int. Cl.$^7$ .................. C07C 43/11; C07C 43/18; C07C 43/20; C07C 41/00; C07C 43/02

(52) U.S. Cl. .............. 568/610; 568/629; 568/630; 568/662; 568/774

(58) Field of Search ............... 568/610, 629, 568/630, 662, 774

(56) References Cited

U.S. PATENT DOCUMENTS

| | | | |
|---|---|---|---|
| 3,471,577 A | * 10/1969 | Haubein et al. | 260/623 |
| 6,235,743 B1 | 5/2001 | Gayer et al. | 514/269 |
| 6,359,133 B2 | 3/2002 | Gayer et al. | 544/319 |
| 2001/0018442 A1 | 8/2001 | Gayer et al. | 514/269 |

OTHER PUBLICATIONS

Justus Liebigs Ann. Chem. 350, (month unavailable) 1906, p. 112, E. Erlenmeyer, R. Fittig, A. V. Baeyer, O. Wallach und J. Volhard.

L. Testaferri et al: "The reactions of unactivated aryl halides with sodium methoxide in HMPA" Tetrahedron., Bd. 39, Nr. 1, 1983, Seiten 193–197, XP002168754 Elsevier Science Publishers, Amsterdam., NL ISSN: 0040–4020 Seite 194, Iinke Spalte, Absatz 2.

* cited by examiner

Primary Examiner—Mukund J. Shah
Assistant Examiner—Zachary C. Tucker
(74) Attorney, Agent, or Firm—Richard E. L. Henderson

(57) ABSTRACT

The invention relates to a novel process for preparing 2-alkyl-3-chlorophenols.

10 Claims, No Drawings

METHOD FOR PRODUCING 2-ALKYL-3-CHLOROPHENOLS

This application was filed under 35 U.S.C. 371, and is the U.S. a national stage of PCT/EP01/04547, filed Apr. 23, 2001.

The invention relates to a novel process for preparing 2-alkyl-3-chlorophenols.

2-Alkyl-3-chlorophenols are intermediates which can be used, for example, for preparing crop protection agents (cf. WO 98/21189).

It is already known that 3-chloro-2-methylphenol can be obtained by reacting 2-chlorotoluene with sodium methoxide in hexamethylphosphoramide (HMPA) as solvent and treatment of the reaction solution with sodium isopropylthiolate. One disadvantage of this process is the use of HMPA as solvent, since it is highly carcinogenic. Also, the sodium isopropylthiolate used and the isopropylthiol released during the work-up are very odorous. For these reasons, this process is not applicable on the industrial scale.

In another process (cf. Justus Liebigs Ann. Chem., 350, 1906, 112), the preparation of 3-chloro-2-methylphenol takes place starting from 2-amino-6-chlorotoluene. Diazotization using nitrous acid and subsequent hydrolysis in a boiling mixture of water and sulphuric acid gives 3-chloro-2-methylphenol.

A significant disadvantage of this process is that the starting material cannot be prepared in isomerically pure form. High levels of by-products are isolated, which results in low yields. Also, the diazonium salt formed is of limited solubility so that the process must be operated in high dilution, which makes the preparation of 3-chloro-2-methylphenol on the industrial scale more difficult. A further disadvantage is that a steam distillation must be carried out, whose operation, particularly on the industrial scale, is costly and inconvenient.

It has been found that 2-alkyl-3-chlorophenols of the general formula (I)

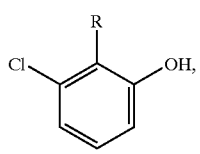
(I)

where
R is $C_1$–$C_6$-alkyl, are obtained
when alkyldichlorobenzene derivatives of the general formula (II)

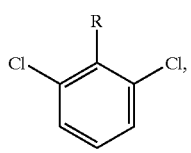
(II)

where
R has the above meanings, are reacted
a1) with a base in a high-boiling organic diluent of the general formula (III)

$R^1$—OH (III), where $R^1$ is
$R^2$—O—$(CH_2)_2$—O—$(CH_2)_2$—,
$R^2$—O—$(CH_2)_2$—O(—$CH_2$)$_2$—O—$(CH_2)_2$—,
$R^2$—O—$(CH_2)_2$—O(—$CH_2$)$_2$—O—$(CH_2)_2$—O—$(CH_2)_2$— or
—$C_6$ to $C_{10}$-alkyl,
where $R^2$ is hydrogen, methyl or ethyl,
optionally in the presence of a catalyst, and the water released by the reaction is continuously removed,
or are reacted
a2) with a base in a high-boiling organic diluent of the general formula (III)

$R^1$—OH (III), where
$R^1$ has the above meanings,
optionally in the presence of a catalyst, and any water released during the reaction is continuously removed,
and the resulting compounds of the formula (IV)

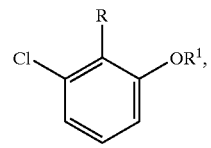
(IV)

where
R and $R^1$ have the above meanings, are treated with relatively highly concentrated acid,
or are reacted
b1) with a base in a primary alcohol having 1 to 3 carbon atoms used as a diluent under pressure,
or are reacted
b2) with a base in a primary alcohol having 1 to 3 carbon atoms used as a diluent under pressure,
and the resulting compounds of the formula (IV)

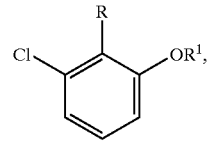
(IV)

where
R and $R^1$ have the above meanings,
are treated with relatively highly concentrated acid.

After operation of the process variants a1) and b1), the reaction mixture is acidified with a dilute acid.

In the compounds of the formula (II), R is in particular methyl, ethyl, n- or i-propyl.

In the compounds of the formula (II), R is more preferably methyl.

In the compounds of the formula (III), $R^1$ is more preferably HO—$(CH_2)_2$—O—$(CH_2)_2$—.

The radical definitions listed above or given as preferred meanings apply both to starting compounds of the formulae (II) and (III) and correspondingly to the final products of the formula (I) and the intermediates of the formula (IV).

The specific radical definitions given for the combinations or combinations of radicals in question are, independently of the combination of the radicals given, alternatively arbitrarily replaced by radical definitions of other preferred meanings.

It is particularly surprising to note that, in the process of the invention, 2-alkyl-3-chlorophenols are obtained in high yields and high purity, since, for other comparable reactions, more drastic reaction conditions, such as hydrolysis to give phenols in a boiling mixture of water and sulphuric acid, are required.

The process of the invention has a whole series of advantages. For instance, 2-alkyl-3-chlorophenols can be prepared using non-carcinogenic solvents and without the reaction having to be carried out at high dilution. Therefore, the novel process is particularly suitable for industrial scale applications.

The compounds of the general formula (IVa) are hitherto unknown and as novel chemical compounds also form part of the subject-matter of the present invention

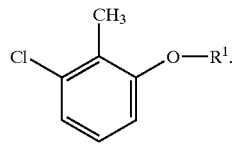

(IV-a)

In the compounds of the formula (IVa),
$R^1$
is $R^2$—O—$(CH_2)_2$—O—$(CH_2)_2$—,
$R^2$—O—$(CH_2)_2$—O—$(CH_2)_2$—O—$(CH_2)_2$—, or
$R^2$—O—$(CH_2)_2$—O—$(CH_2)_2$—O—$(CH_2)_2$—O—$(CH_2)_2$—,
where $R^2$ is hydrogen, methyl or ethyl.

In the compounds of the formula (IVa), $R^1$ is more preferably HO—$(CH_2)_2$—O—$(CH_2)_2$—.

The alkyldichlorobenzene derivatives of the general formula (II) and all other starting compounds are currently commercially available products or can be prepared from these by simple processes.

Examples of preferred diluents of the general formula (III) for operating the process variants a1) and a2) include diethylene glycol, triethylene glycol, tetraethylene glycol or higher-boiling primary alcohols. The process variants a1) and a2) are preferably carried out using diethylene glycol.

The process variants a1) and a2) of the invention are operated in the presence of a suitable acid acceptor. Examples of preferred acid acceptors include alkaline earth metal or alkali metal hydroxides, alkoxides or carbonates, such as sodium methoxide, potassium tert-butoxide, sodium hydroxide, potassium hydroxide, sodium carbonate and potassium carbonate. The process variants a1) and a2) are preferably carried out using sodium hydroxide or, in particular, potassium hydroxide.

The process variants a1) and a2) of the invention are optionally carried out in the presence of a suitable catalyst. Preferred catalysts include tertiary amines, such as trimethylamine, triethylamine, tributylamine, N,N-dimethylaniline, N,N-dimethylbenzylamine, pyridine, picoline, 2-methyl-5-ethylpyridine, N-methylpiperidine, N-methylmorpholine, N,N-dimethylaminopyridine, diazabicyclooctane (DABCO), diazabicyclononene (DBN) or diazabicycloundecene (DBU).

The process variant a1) of the invention is operated using dilute acids, in particular mineral acids, preferable examples of which include sulphuric acid, phosphoric acid, and in particular hydrochloric acid.

The process variant a2) of the invention is preferably carried out using more highly concentrated acids, in particular mineral acids, preferable examples of which include sulphuric acid or hydrochloric acid or hydrobromic acid; and also Lewis acids, preferable examples of which include aluminium trichloride, boron trichloride or boron tribromide. The process variant a2) is preferably carried out using sulphuric acid.

The reaction temperatures during the operation of the process variant a1) of the invention can be varied within a relatively wide range. In general, operation is effected at temperatures of from 100 to 250° C., preferably at temperatures of 160 to 230° C., more preferably at temperatures of 180 to 220° C.

The reaction temperatures during the operation of the process variant a2) of the invention can be varied within a relatively wide range. In general, operation is effected at temperatures of from 100 to 250° C., preferably at temperatures of from 120 to 230° C., more preferably at temperatures of from 140 to 200° C.

The process variants a1) and a2) of the invention are generally operated under atmospheric pressure. However, it is also possible to work under pressure, in general from 1 bar to 10 bar.

To operate the process variant a1) of the invention for preparing the compounds of the formula (I), generally from 2 to 10 mol, preferably from 2 to 4 mol of base are used per mole of the compounds of the formula (II).

To carry out the process variant a2) of the invention for preparing the compounds of the formula (I), generally from 1 to 10 mol, preferably from 1 to 3 mol of base are used per mole of the compounds of the formula (II).

The operation of the process variant a1) of the invention is generally effected as follows: the alkyldichlorobenzene derivatives of the general formula (II) are heated with a base in the presence of a diluent, and the water released by the reaction is continuously distilled off. The work-up is carried out by acidifying the reaction mixture with an acid and working it up by customary methods.

The operation of the process variant a2) of the invention is generally effected as follows: the alkyldichlorobenzene derivatives of the general formula (II) are heated with a base in the presence of a diluent, and the water released by the reaction is continuously distilled off, and the reaction mixture is worked up by customary methods. The compounds of the formula (IV) obtained are treated with acid, and the reaction mixture is worked up by customary methods.

Useful diluents for operating the process variants b1) and b2) of the invention include primary alcohols, such as methanol, ethanol, n-propanol or i-propanol, or mixtures thereof with water. The process variants b1) and b2) are preferably carried out using methanol.

The process variants b1) and b2) of the invention are operated in the presence of a suitable acid acceptor. Useful acid acceptors include all customary inorganic and organic bases. Preferable examples include alkaline earth metal or alkali metal hydroxides, alkoxides or carbonates, such as sodium methoxide, potassium tert-butoxide, sodium hydroxide, potassium hydroxide, sodium carbonate or potassium carbonate. The process variants b1) and b2) are preferably carried out using sodium hydroxide or, in particular potassium hydroxide.

To operate the process variant b1) of the invention, dilute acids, in particular mineral acids, are used, preferred examples of which include sulphuric acid, phosphoric acid, and in particular hydrochloric acid.

To operate the process variant b2) of the invention, more highly concentrated acids, in particular mineral acids, are used, preferable examples of which include sulphuric acid or hydrochloric acid or hydrobromic acid; and also Lewis acids, preferable examples of which include aluminium trichloride, boron trichloride and boron tribromide. The process variant a2) is preferably carried out using sulphuric acid.

The reaction temperatures during the operation of the process variant b1) of the invention can be varied within a relatively wide range. In general, operation is effected at temperatures of from 170 to 250° C., preferably at temperatures of from 180 to 220° C.

The reaction temperatures during the operation of the process variants b2) of the invention can be varied within a relatively wide range. In general, operation is effected at temperatures of from 100 to 220° C., preferably at temperatures of from 150 to 200° C.

The process variants b1) and b2) of the invention are generally operated under elevated pressure. In general, operation is effected at pressures of from 1 to 130 bar, in particular at pressures of from 10 to 40 bar.

To operate the process variant b1) of the invention for preparing the compounds of the formula (I), generally from 2 to 10 mol, preferably from 2 to 4 mol of base, are used per mole of the compounds of the formula (II).

To operate the process variant b2) of the invention for preparing the compounds of the formula (I), generally from 1 to 10 mol, preferably from 1 to 3 mol of base, are used per mole of the compounds of the formula (II).

Operation of the process variant b1) of the invention is generally effected as follows: the alkyldichlorobenzene derivatives of the general formula (II) are heated with a base in the presence of a diluent under pressure. After the end of the reaction, the reaction mixture is acidified with an acid and worked up by customary methods.

Operation of the process variant b2) of the invention is generally carried out as follows: the alkyldichlorobenzene derivatives of the general formula (II) are heated with a base in the presence of a diluent under pressure. The compounds of the formula (IV) obtained are treated with acid, and the reaction mixture is worked up by customary methods.

The process variant a1) of the invention is particularly preferred.

The process of the invention is used in particular for preparing 3-chloro-2-methylphenol, which is an important intermediate for preparing pesticides (cf. WO 98/21189). By the process of the invention, 3-chloro-2-methylphenol is obtained in constantly high purities and good yields. The novel process therefore makes the preparation of known pesticides easier.

The following examples serve to illustrate the invention. However, the invention is not limited to the examples.

EXAMPLES

Example 1

3-Chloro-2-methylphenol

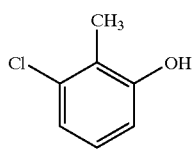

(I-1)

Process Variant a1)

16.1 g (0.1 mol) of 2,6-dichlorotoluene and 19.8 g (0.3 mol) of potassium hydroxide (85%) are heated in 30 ml of diethylene glycol at a bath temperature of 190° C. for 18 hours. The water released by the reaction is distilled off. After cooling, the reaction mixture is stirred with 100 ml of water until a solution is obtained and extracted three times with 50 ml of dichloromethane. The aqueous phase is admixed with 35 ml of 30% hydrochloric acid and extracted three times with 70 ml of dichloromethane. The organic phases are dried over sodium sulphate and concentrated under reduced pressure. 3-Chloro-2-methylphenol is obtained as a solid (12.4 g, content by HPLC: 83%, 72% of theory).

NMR (d$^6$-DMSO): 6.75 (d, 1H, aromatic), 6.85 (d, 1H, aromatic) 7.0 (t, 1H, aromatic), 9.8 (s, 1H, phenolic OH).

Example 2

3-Chloro-2-methylphenol

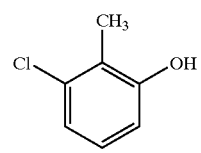

(I-1)

Process Variant a1)

16.1 g (0.1 mol) of 2,6-dichlorotoluene, 19.8 g (0.3 mol) of potassium hydroxide (85%) and 0.3 g of dibenzo-18-crown-6 are heated in 30 ml of diethylene glycol at a bath temperature of 190° C. with reflux for 16 hours. The water released during the reaction is distilled off. After cooling, the reaction mixture is stirred with 100 ml of water until a solution is obtained and extracted three times with 50 ml of dichloromethane. The aqueous phase is admixed with 35 ml of 30% hydrochloric acid and extracted three times with 70 ml of dichloromethane. The organic phases are dried and concentrated under reduced pressure. 3-Chloro-2-methylphenol is obtained as a solid (11.5 g, content by HPLC: 97%, 78% of theory).

Example 3

3-Chloro-2-methylphenol

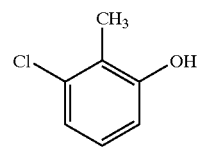

(I-1)

Process Variant b1

8.1 g (0.05 mol) of 2,6-dichlorotoluene and 9.9 g (0.15 mol) of potassium hydroxide (85%) are heated in 40 ml of methanol in an autoclave at 200° C. for 20 hours, which results in a pressure of 30 bar. After cooling, the reaction mixture is poured into 250 ml of water and extracted three times with 70 ml of dichloromethane. The aqueous phase is acidified to pH 1–2 with 30% hydrochloric acid and again extracted three times with 70 ml of dichloromethane each time. The united organic phases are dried over sodium sulphate and evaporated under reduced pressure to give a solid. 3-Chloro-2-methylphenol is obtained as a solid (6.2 g, content by HPLC: 93.5%, 82% of theory).

Example 4

3-Chloro-2-methylanisole

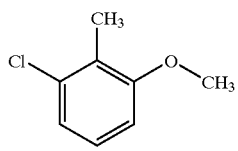
(IVa-1)

Process Variant b2)—First Step—Preparation of Compounds of the Formula (IVa-1)

8.1 g (0.05 mol) of 2,6-dichlorotoluene and 9.9 g (0.15 mol) of potassium hydroxide (85%) are heated in 40 ml of methanol in an autoclave at 160° C. for 20 hours, and the pressure rises to about 12 bar. After cooling, the reaction mixture is poured into about 250 ml of water and extracted three times with about 70 ml of dichloromethane. The united organic phases are dried over sodium sulphate and evaporated under reduced pressure. 3-Chloro-2-methylanisole is obtained as an oil (2.5 g, GC analysis: 37.1%, 12% of theory).

Ret. index GC: 1187, m/e: 156 NMR ($d^6$-DMSO) ppm: 2.2 (s, 3H, $CH_3$), 3.8 (s, 3H, O—$CH_3$), 6.95 (d, 1H, aromatic), 7.0 (d, 1H, aromatic), 7.2 (t, 1H, aromatic)

3-Chloro-2-methylphenol

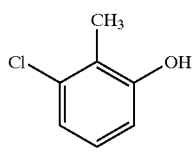
(I-1)

Process Variant b2)—Second Step—Preparation of Compounds of the Formula (I-1)

3.1 g (0.02 mol) of 3-chloro-2-methylanisole are heated in 20 ml of 50% sulphuric acid for 18 hours with reflux. After cooling, the reaction mixture is extracted three times with dichloromethane, dried over sodium sulphate and concentrated to dryness under reduced pressure. 3-Chloro-2-methylphenol is obtained as a solid (2.9 g, content by HPLC: 11.7%, 12% of theory).

Example 5

2-Chloro-6-[2-(2-hydroxyethoxy)-ethoxy]toluene

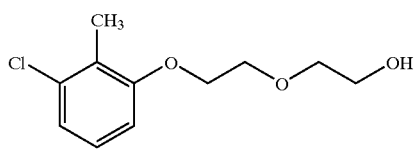
(IVa-2)

Process Variant b2)—First Step—Preparation of Compounds of the Formula (IVa-2)

4 g (0.025 mol) of 2,6-dichlorotoluene and 2.4 g (0.036 mol) of potassium hydroxide (85%) are heated in 10 ml of diethylene glycol for four hours under reflux. After cooling, the reaction mixture is stirred vigorously with water and extracted three times with dichloromethane. The organic phases are dried over sodium sulphate and are concentrated under reduced pressure. 2–Chloro-6-[2-(2-hxdroxyethoxy)-ethoxy]toluene is obtained as an oil (2.7 g, GC analysis: 32.3%, 15% of theory).

Ret. index GC: 1776, m/e: 230 NMR ($d^6$-DMSO) ppm: 2.2 (s, 3H, $CH_3$), 3.5 (m, 4H, $CH_2$), 3.8 (m, 2H, $CH_2$), (4.1, m, 2H, $CH_2$), 4.6 (m, 1H, OH), 6.9–7.2 (m, 3H, aromatic H).

What is claimed is:

1. A process for preparing a compound of the formula (I)

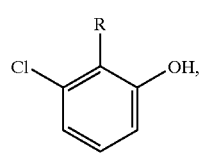
(I)

where R is $C_1$–$C_6$-alkyI, comprising (a) reacting a compound of the formula (II)

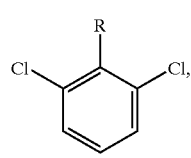
(II)

where R has the above meanings, with (a1) a base in a high-boiling organic diluent of the formula (III)

$R^1$—OH  (III), where $R^1$ is $R^2$—O—$(CH_2)_2$—O—$(CH_2)_2$—, $R^2$—O—$(CH_2)_2$—O (—$CH_2)_2$—O—$(CH_2)_2$—, $R^2$—O—$(CH_2)_2$—O(—$CH_2)_2$—O—$(CH_2)_2$—O—$(CH_2)_2$—, or $C_6$ to $C_{10}$-alkyl, where $R^2$ is hydrogen, methyl, or ethyl, optionally in the presence of a catalyst, wherein the water released by the reaction is continuously removed, to form a reaction mixture that is acidified with a dilute acid, or (a2) a base in a high-boiling organic diluant of the formula (III)

$R^1$—OH  (III), where $R^1$ has the above meanings, optionally in the presence of a catalyst, wherein any water released during the reaction is continuously removed, to form a compound of the formula (IV)

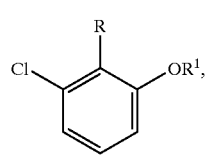
(IV)

where R and $R^1$ have the above meanings, that is then treated with a relatively highly concentrated acid, or (b) reacting a compound of the formula (II)

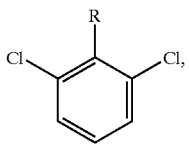
(II)

where R has the above meanings, with
- (b1) a base in a primary alcohol having 1 to 3 carbon atoms used as a diluent under pressure, to form a reaction mixture that is acidified with a dilute acid, or
- (b2) a base in a primary alcohol having 1 to 3 carbon atoms used as a diluent under pressure, to form a compound or the formula (IV)

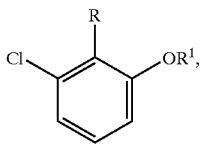
(IV)

where
R has the above meanings, and
$R^1$ is the residue of a primary alcohol having 1 to 3 carbon atoms, that is then treated with a relatively highly concentrated acid.

2. A process according to claim 1 wherein the diluent used in the process variants (a1) and (a2) is diethylene glycol.

3. A process according to claim 1 wherein the diluent used in the process variants (b1) and (b2) is methanol.

4. A process according to claim 1 wherein the process variants (a1) and (a2) are carried out at temperatures of from 100° C. to 250° C.

5. A process according to claim 1 wherein the process variant (b1) is carried out at temperatures of from 170° C. to 250° C.

6. A process according to claim 1 wherein the process variant (b2) is carried out at temperatures of from 100° C. to 220° C.

7. A process according to claim 1 wherein the process variant (a1) is carried out as a one-pot process.

8. A process according to claim 1 wherein the base is potassium hydroxide.

9. A compound of the formula (IV-a)

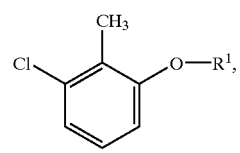
(IV-a)

where $R^1$ is $R^2$—O—$(CH_2)_2$—O—$(CH_2)_2$—, $R^2$—O—$(CH_2)_2$—O—$(-CH_2)_2$—O—$(CH_2)_2$—, $R^2$—O—$(CH_2)_2$—O(—$CH_2)_2$—$(CH_2)_2$—O—$(CH_2)_2$—, or $C_6$ to $C_{10}$-alkyl, where $R^2$ is hydrogen, methyl, or ethyl.

10. A compound of the formula (IVa-2)

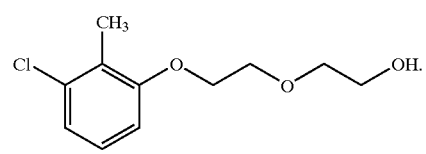
(IVa-2)

* * * * *